(12) United States Patent
Metodiev et al.

(10) Patent No.: US 11,384,080 B2
(45) Date of Patent: Jul. 12, 2022

(54) METHOD FOR ISOLATION OF CYTISINE

(71) Applicant: SOPHARMA AD, Sofia (BG)

(72) Inventors: Danail Georgiev Metodiev, Sofia (BG); Maria Nedkova Klisarova, Sofia (BG); Petya Mitkova Apostolova, Sofia (BG); Galina Nikolova Zaekova, Sofia (BG); Nikolay Kirilov Stoyanov, Sofia (BG)

( * ) Notice: Subject to any disclaimer, the term of this patent is extended or adjusted under 35 U.S.C. 154(b) by 0 days.

(21) Appl. No.: 17/344,090

(22) Filed: Jun. 10, 2021

(65) Prior Publication Data
US 2021/0300929 A1 Sep. 30, 2021

Related U.S. Application Data

(63) Continuation of application No. 16/965,790, filed as application No. PCT/BG2018/000044 on Nov. 19, 2018.

(30) Foreign Application Priority Data

Jan. 29, 2018 (BG) ........................................ 112671

(51) Int. Cl.
*C07D 471/18* (2006.01)
*B01D 11/04* (2006.01)

(52) U.S. Cl.
CPC ........ *C07D 471/18* (2013.01); *B01D 11/0492* (2013.01)

(58) Field of Classification Search
None
See application file for complete search history.

(56) References Cited

FOREIGN PATENT DOCUMENTS

| CN | 101891740 | 11/2010 |
| CN | 107266448 | 10/2017 |

OTHER PUBLICATIONS

Xiaoyin Wang, Chemical Abstract 154: 26853, Abstract of CN 10189740 (Year: 2010).*
Daqi Wang, Chemical Abstracts 167:552554, Abstract of CN 107266448 (Year: 2017).*
Goina T. et al., "Neue Beitrage Zum Problem Der Extraktion Des Cytisins [New Contribution to the Extraction of Cytisine]" Planta Medica, Thieme Verlag, DE, 20(4):116 (publication date: Sep. 1, 1971) (with English translation).
International Search Report and Written Opinion dated Feb. 25, 2019 for PCT/BG2018/000044.

* cited by examiner

*Primary Examiner* — Zinna Northington Davis
(74) *Attorney, Agent, or Firm* — Perkins Coie LLP

(57) ABSTRACT

The invention concerns a method for isolation of cytisine from plant material. The method according to the invention, consists in extraction of the plant raw material by lower alcohol, acidified with mineral acid to pH within a range 1.5-3.5. The combined alcohol-aqueous extracts are concentrated under vacuum distillation till the alcohol is eliminated and after filtration they are extracted with chloroform, methylene chloride, butyl acetate or normal butanol in a ratio of 1:1. The purified from ballast substances acid aqueous concentrate is alkalized to pH 9-12 with alkaline hydroxide or ammonium hydroxide and the resulting alkaline aqueous concentrate is extracted at least twice with chloroform, methylene chloride, butyl acetate or normal butanol in a ratio of concentrate:extractant of 1:5 to 1:10. The combined organic extracts are evaporated to dryness, then acetone or ethyl acetate are added to obtain a suspension which is allowed to crystallize completely at 5-10° C., then it is filtered and dried. The isolated product is with a high purity and yield.

21 Claims, No Drawings

METHOD FOR ISOLATION OF CYTISINE

CROSS-REFERENCE TO RELATED APPLICATIONS

This application is a continuation of U.S. patent application Ser. No. 16/965,790 filed Jul. 29, 2020, which is a U.S. 371 national phase entry of International Application No. PCT/BG2018/000044 filed Nov. 19, 2018, which claims the benefit of Bulgaria Patent Application No. 112671 filed Jan. 29, 2018, the contents of which are herein incorporated in their entirety.

TECHNICAL FIELD

The invention concerns a method for isolating cytisine from plant material.

BACKGROUND

Cytisine-(R,5S)-1,2,3,4,5,6-hexahydro1,5-methano-8H-pyrido[1,2-α] (1,5) diazocin-8-one, with the following configuration:

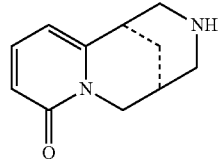

is a potent nicotinic acetylcholine receptor agonist that shows pharmacological effects similar to nicotine. It is used in fighting nicotine and alcohol dependence. Its presence has been established in various plant species like Faboideae subfamily that includes Laburnum, Anagyris, Thermopsis, Cytisus, Genista and Sophora. Cytisine is also found in Gymnocladus, a member of Caesalpinioideae subfamily, etc. Extraction of cytisine from Laburnum seeds was reported more than a century ago (1). Cytisine was later extracted by processing milled seeds with alkali to the obtaining of a paste extracted for several hours using Soxhlet apparatus (2). The proposal includes the use of a mixture of dichloromethane, methanol and ammonium hydroxide (25%) for extraction of cytisine in two similar variants (3) and (4). A method for isolation of alkaloids from a mixture of biomaterial with 0.1 N HCl and subsequent elution of ion-exchange resin was described (5). A method is known for isolation of cytisine from biomaterials, which includes extraction of aqueous alkaline solution (carbonate, hydrogen carbonate or hydroxide of alkaline metal or ammonium hydroxide) of the biomaterial with plant oil (rapeseed oil, sunflower oil, flax oil, grape oil, peanut oil, etc.), re-extraction in acid-aqueous phase (preferably with sulfuric acid), recovery of cytisine by alkaline extraction with dichloromethane (dichloromethane plus ammonium), removal of water and evaporation of the solvent. However, the purity of cytisine obtained in the above examples is very low (28%) (6). There is a semisynthetic method for obtaining alkaloid derivatives of cytisine for treatment of CNS diseases, the initial stage consisting of maceration of powdered Ormosia, powdered roots and stems in particular, in methanol, followed by filtration and evaporation to dryness; distribution of the obtained extract between water solution of hydrochloric acid and ethyl acetate; separation of water and organic phases; alkalization of the aqueous phase to pH 10-12 with sodium carbonate; addition of dichloromethane; and repeated separation of phases and isolation of compounds which are later subjected to chemical reactions to the obtaining of the target products (7). A method for extraction of cytisine from thermopsis lanceolate has been protected as well (8).

It is evident from the overview that the matter of cytisine extraction from plants, although with a long history, has not received a satisfactory solution. The known approaches for isolation of cytisine are multistage, labour-intensive, low-effective and result in a product with very low purity. This determines the great need of a method that ensures good yield of cytisine with higher purity—a need imposed by the increasing search and the expanding usage application of this alkaloid.

SUMMARY

It was established that from cytisine-containing plant material, using an accessible and efficient method, cytisine with high yield and purity grade of an active pharmaceutical ingredient (API) could be obtained. The method, according to the invention, includes extraction of the plant raw material with a lower alcohol (preferably methanol or ethanol), acidified with a mineral acid to pH in the range 1.5-3.5 and temperature of 20-50° C. The combined alcohol-aqueous extracts which include 50-80% of lower alcohol are concentrated under vacuum to eliminate the alcohol, and after filtration they are extracted with chloroform, methylene chloride, butyl acetate or normal butanol in a ratio of 1:1. The acidified aqueous concentrate thus purified from ballast substances is alkalized to pH 9-12 with alkaline (sodium or potassium) hydroxide or ammonium hydroxide and the alkaline aqueous concentrate is extracted at least twice with chloroform, methylene chloride, butyl acetate or normal butanol in a ratio of concentrate:extractant from 1:5 to 1:10. The combined organic extracts are evaporated to dryness, then acetone or ethyl acetate are added to obtain a suspension that is allowed to crystallize completely at 5-10° C., then it is filtered and it is dried. The use of the simple and elegant method, according to the invention, surprisingly obtained Cytisine HPLC grade of 98-99.9%, and yield of 80-85%.

The use of the simple and elegant method according to the invention surprisingly obtained a Cytisine HPLC grade of 98-99.9% and a yield of 80-85%.

The following example's illustrate the essence of the method according to the invention, without limiting it.

EXAMPLES

Example 1: Preparation of Cytisine by Acid Methanol Extraction of Milled Seeds of Golden Chain Tree (Cytisus laburnum L., Golden Chain)

15 kg of milled seeds of Golden Chain tree (Cytisus laburnum L.) are extracted twice, each with 45 L of acidified with 0.350 L of sulfuric acid 70% methanol for 5 hours at pH 2.5-3 and temperature of 30° C. The combined alcohol-aqueous acid extracts are concentrated under vacuum to a volume of 25 L (1/5) of the initial volume, the solid components are removed by filtration and the obtained concentrate is twice extracted with 10 L of chloroform each at pH range of 2.5-3.0. The obtained purified acid aqueous concentrate is alkalized with 30% sodium hydroxide solution to pH 11, then it is extracted five times each extraction with 25 L of chloroform. The combined organic extracts are subjected to distillation until the chloroform is completely eliminated and 2 L of acetone is added to the obtained residue to obtain an acetone suspension which rested for 11 hours at 5-10° C., then is filtered and it is dried.

127 g of Cytisine with HPLC grade of 99.15% and yield of 85% are obtained.

Example 2: Preparation of Cytisine by Acid Methanol Extraction of Milled Seeds of Golden Chain Tree (*Cytisus laburnum* L., Golden Chain)

As in Example 1, the milled seeds of Golden Chain tree (*Cytisus laburnum* L.). are extracted with 60% methanol, acidified with hydrochloric acid. The acid aqueous concentrate is purified with chloroform, according to Example 1, alkalized with 25% of sodium hydroxide solution to pH 11, and then it is extracted seven times each with 20 L of methylene chloride. The combined organic extracts are subjected to distillation until the methylene chloride is completely eliminated and 2 L of acetone is added to the obtained residue to obtain acetone suspension which rested for 10 hours at 5-10° C., then the obtained precipitate is filtered and it is dried.

121.5 g, of Cytisine HPLC grade of 98.72% and yield of 81% are obtained.

Example 3: Preparation of Cytisine by Acid Methanol Extraction of Milled Seeds of Golden Chain Tree (*Cytisus laburnum* L., Golden Chain)

As in Example 1, the milled seeds of Golden Chain tree (*Cytisus laburnum* L.) are extracted with 70% ethanol acidified with sulfuric acid, instead of acid methanol. The acid aqueous concentrate, purified with chloroform, is alkalized according to Example 1, with 25% of ammonium hydroxide solution to pH 11, then it is extracted six times each with 25 L of chloroform. The obtained chloroform extracts are further treated as in Example 1.

125 g of Cytisine HPLC grade of 98.7% and yield of 83% are obtained.

Example 4: Preparation of Cytisine by Acid Ethanol Extraction of Milled Seeds of Golden Chain Tree (*Cytisus laburnum* L., Golden Chain)

As in Example 1, the milled seeds of Golden Chain tree (*Cytisus laburnum* L.) are extracted with acidified with sulfuric acid 70% ethanol instead of acid methanol.

The acid aqueous concentrate is purified with chloroform using 40% of sodium hydroxide solution to pH 11, then it is extracted five times each with 25 L of chloroform. The obtained chloroform extracts are further treated as in Example 1.

120 g of Cytisine HPLC grade of 98.3% and yield of 80% are obtained.

Example 5: Preparation of Cytisine by Acid Methanol Extraction of Milled Seeds of Golden Chain Tree (*Cytisus laburnum* L., Golden Chain)

15 kg of milled seeds of Golden Chain tree (*Cytisus laburnum* L.) are extracted three times each with 45 L of acidified with 1.09 L of hydrochloric acid 80% ethanol, for 5 hours at pH 2.5-3.0 and temperature of 28° C. The combined alcohol-aqueous acid extracts are concentrated under vacuum to a volume of 20 L, the acid concentrate is filtered, then it is extracted twice each with 10 L of methylene chloride at pH range of 2.5-3.0. The acid purified aqueous concentrate is alkalized with sodium hydroxide to pH 11, then it is extracted six times each with 20 L of methylene chloride. The combined organic extracts are subjected to distillation until the methylene chloride is completely eliminated and 2 L of ethyl acetate is added to the obtained residue to obtain ethyl acetate suspension, stirred at 5-10° C. and allowed to stay at rest for 10 hours, then the obtained precipitate is filtered and it is also dried.

119 g of Cytisine HPLC grade of 98.8% and yield of 79% are obtained.

Example 6: Preparation of Cytisine by Acid Methanol Extraction of Milled Seeds of Golden Chain Tree (*Cytisus laburnum* L., Golden Chain)

15 kg of milled seeds of Golden Chain tree (*Cytisus laburnum* L.) are extracted three times each with 45 L of acidified with 0.350 L of sulfuric acid 70% methanol for 5 hours at pH 2.5-3 and temperature of 30° C. The combined alcohol-aqueous acid extracts are concentrated under vacuum to a volume of 25 L (1/5) of the initial volume, the solid components are removed by filtration and the obtained concentrate is extracted twice each with 10 L of butyl acetate at pH range of 2.6-3.0. The acid purified aqueous concentrate is alkalized with 30% of sodium hydroxide solution to pH 11, then it is extracted six times each with 25 L of butyl acetate. The combined organic extracts are subjected to distillation until the butyl acetate is completely eliminated and 2 L of acetone is added to the obtained residue, which is left at rest for 11 hours at 5-10° C. to obtain aimed acetone suspension, then it is filtered and it is dried.

125 g of Cytisine HPLC grade of 99.85% and yield of 81% are obtained.

Example 7: Preparation of Cytisine by Acid Methanol Extraction of Milled Seeds of Golden Chain Tree (*Cytisus laburnum* L., Golden Chain)

15 kg of milled seeds of Golden Chain tree (*Cytisus laburnum* L.) are extracted three times each with 45 L of acidified with 0.350 L of sulfuric acid 70% methanol for 5 hours at pH 2.5-3 and temperature of 30° C. The combined alcohol-aqueous acid extracts are concentrated under vacuum to a volume of 25 L (1/5) of the initial volume, the solid components are removed by filtration and the obtained concentrate is extracted twice each with 10 L of n-butanol at pH range of 2.5-3.0. The acid purified aqueous concentrate is alkalized with 30% sodium hydroxide solution to pH 11, then it is extracted six times each with 25 L of n-butanol. The combined n-butanol extracts are further treated as in Example 6.

120 g of Cytisine HPLC grade of 99.66% and yield of 82% are obtained.

Example 8: Preparation of Cytisine by Acid Methanol Extraction of Milled Seeds of *Thermopsis* (*Thermopsis lanceolate* R.Br)

15 kg of powdered seeds of *Thermopsis* (*Thermopsis lanceolate* R.Br) are extracted three times each with 45 L of acidified with 0.350 L of sulfuric acid 70% methanol for 5 hours at pH 2.5-3.0 and temperature of 30° C. The combined alcohol-aqueous acidified extracts are concentrated under vacuum to a volume of 25 L (1/5) of the initial volume, the solid components are removed by filtration and the obtained concentrate is extracted twice each with 10 L of n-butanol at pH range of 2.5-3.0. The acid purified aqueous concentrate is alkalized with 30% sodium hydroxide solution to pH 11, then it is extracted six times each with 25 L of n-butanol. The combined n-butanol extracts are further treated as in Example 6.

121 g of Cytisine HPLC grade of 99.32% and yield of 81% are obtained.

Example 9: Preparation of Cytisine by Acid Ethanol Extraction of Milled Seeds of *Thermopsis* (*Thermopsis lanceolata* R. Br)

15 kg of milled seeds of *Thermopsis* (*Thermopsis lanceolata* R.Br) are extracted three times each with 45 L of acidified with 1.09 L of hydrochloric acid 80% ethanol for 5 hours at pH 2.5-3 and temperature of 28° C. The combined alcohol-aqueous acidified extracts are concentrated under vacuum to a volume of 20 L, the acid concentrate is filtered, then it is extracted twice each with 10 L of methylene chloride at pH range of 2.5-3.0. The acid purified aqueous concentrate is alkalized with sodium hydroxide to pH 12, then it is extracted six times each with 20 L of methylene chloride. The combined organic extracts are subjected to distillation until the methylene chloride is completely eliminated and 2 L of ethyl acetate is added to the obtained residue to obtain ethyl acetate suspension, stirred at 5-10° C., allowed to stay at rest for 12 hours, then it is filtered and the obtained precipitate is dried.

120 g of Cytisine HPLC grade of 98.9% and yield of 80% are obtained.

We claim:

1. A method for isolating cytisine from raw plant material, the method comprising:
   (a) dissolving the raw plant material in a $C_1$ or $C_2$ alcohol to form a liquid mixture;
   (b) acidifying the liquid mixture by addition of a mineral acid to obtain an aqueous solution;
   (c) removing the $C_1$ or $C_2$ alcohol for the liquid mixture to form a concentrated aqueous solution;
   (d) extracting the concentrated aqueous solution with an extractant to form a purified aqueous concentrate;
   (e) alkalizing the purified aqueous concentrate with an alkaloid to form an alkaline aqueous concentrate;
   (f) extracting the alkaline aqueous concentrate with an extractant; and
   (g) removing the extractant to obtain cytisine.
2. The method of claim 1, further comprising crystallizing cytisine in an organic solvent.
3. The method of claim 2, wherein crystallizing further comprises filtering cytisine from the organic solvent.
4. The method of claim 3, wherein the organic solvent is acetone or ethyl acetate.
5. The method of claim 1, further comprising filtering the concentrated aqueous solution after removing the $C_1$ or $C_2$ alcohol.
6. The method of claim 1, wherein extracting the concentrated aqueous solution with an extractant comprises adding an extractant, wherein a ratio of the concentrated aqueous solution to the extractant is 1:1.
7. The method of claim 1, wherein extracting the alkaline aqueous concentrate with an extractant comprises adding an extractant, wherein a ratio of the alkaline aqueous concentrate to the extractant is about 1:5 to about 1:10.
8. The method of claim 1, wherein the $C_1$ or $C_2$ alcohol is methanol or ethanol.
9. The method of claim 1, wherein a pH of the aqueous solution after addition of the mineral acid is between about 1.5 and about 3.5.
10. The method of claim 1, wherein the mineral acid is sulfuric acid or hydrochloric acid.
11. The method of claim 1, wherein the extractant is one or more of chloroform, methylene chloride, butyl acetate, or n-butanol.
12. The method of claim 1, wherein the alkaloid is sodium hydroxide or ammonium hydroxide.
13. The method of claim 1, wherein a pH of the purified aqueous concentrate is about 9 to about 12 after addition of the alkaloid.
14. The method of claim 1, wherein the concentrated aqueous solution is extracted about six times.
15. The method of claim 2, wherein cytisine is obtained at a purity of at least about 98%.
16. The method of claim 3, wherein cytisine is obtained at a purity of at least about 98%.
17. The method of claim 2, wherein cytisine is obtained at a purity of at least about 99%.
18. The method of claim 3, wherein cytisine is obtained at a purity of at least about 99%.
19. The method of claim 1, wherein a yield of cytisine is at least about 80%.
20. The method of claim 19, wherein the yield of cytisine is at least about 85%.
21. The method of claim 1, wherein (d) extracting the concentrated aqueous solution with the extractant to form the purified aqueous concentrate is performed at a temperature ranging from 20° C. to 50° C.

\* \* \* \* \*